(12) United States Patent
Sato et al.

(10) Patent No.: US 9,039,178 B2
(45) Date of Patent: May 26, 2015

(54) IMAGE PROCESSING APPARATUS AND IMAGE PROCESSING METHOD

(71) Applicant: CANON KABUSHIKI KAISHA, Tokyo (JP)

(72) Inventors: Makoto Sato, Tokyo (JP); Tomoyuki Makihira, Tokyo (JP); Yoshihiko Iwase, Kyoto (JP); Kazuhide Miyata, Yokohama (JP); Hiroyuki Shinbata, Tama (JP); Ritsuya Tomita, Yokohama (JP); Daisuke Kibe, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 31 days.

(21) Appl. No.: 13/972,159

(22) Filed: Aug. 21, 2013

(65) Prior Publication Data

US 2014/0055745 A1    Feb. 27, 2014

(30) Foreign Application Priority Data

Aug. 27, 2012    (JP) ................................. 2012-186590

(51) Int. Cl.
   *A61B 3/10*    (2006.01)
(52) U.S. Cl.
   CPC ...................................... *A61B 3/102* (2013.01)
(58) Field of Classification Search
   USPC .......................... 351/206, 246, 221, 205, 200
   See application file for complete search history.

(56) References Cited

U.S. PATENT DOCUMENTS

| | | |
|---|---|---|
| 2007/0070295 A1 | 3/2007 | Tsukada et al. |
| 2008/0151187 A1* | 6/2008 | Tsukada et al. ............... 351/206 |
| 2009/0115964 A1 | 5/2009 | Ueno |
| 2012/0120368 A1* | 5/2012 | Fujimora et al. ............... 351/206 |
| 2012/0147326 A1* | 6/2012 | Yatagai et al. ................ 351/206 |

FOREIGN PATENT DOCUMENTS

WO    2010122118 A1    10/2010

OTHER PUBLICATIONS

G•Tzinger, E., et al., "Retinal nerve fiber layer birefringence evaluated with polarization sensitive spectral domain OCT and scanning laser polarimetry: A comparison", Journal of Biophotonics, Feb. 18, 2008, pp. 129-139, vol. 1, No. 2.

G•Tzinger, E., et al., "Retinal pigment epithelium segmentation by polarization sensitive optical coherence tomography", Optical Society of America, Oct. 15, 2008, vol. 16, No. 21.

* cited by examiner

*Primary Examiner* — Hung Dang
(74) *Attorney, Agent, or Firm* — Canon USA Inc. IP Division

(57) ABSTRACT

This image processing apparatus includes: a planar image acquisition unit configured to acquire a planar image showing a polarization state of a subject, a tomographic image acquisition unit configured to acquire a three-dimensional tomographic image including a plurality of two-dimensional tomographic image of the subject, a display control unit configured to display, on the display unit, an index indicating a position of a tomographic image to be displayed on the display unit among a plurality of two-dimensional tomographic images, by superimposing it on a planar image showing the polarization state, and an instruction unit configured to give an instruction to change a position of the index on a planar image showing the polarization state.

16 Claims, 13 Drawing Sheets

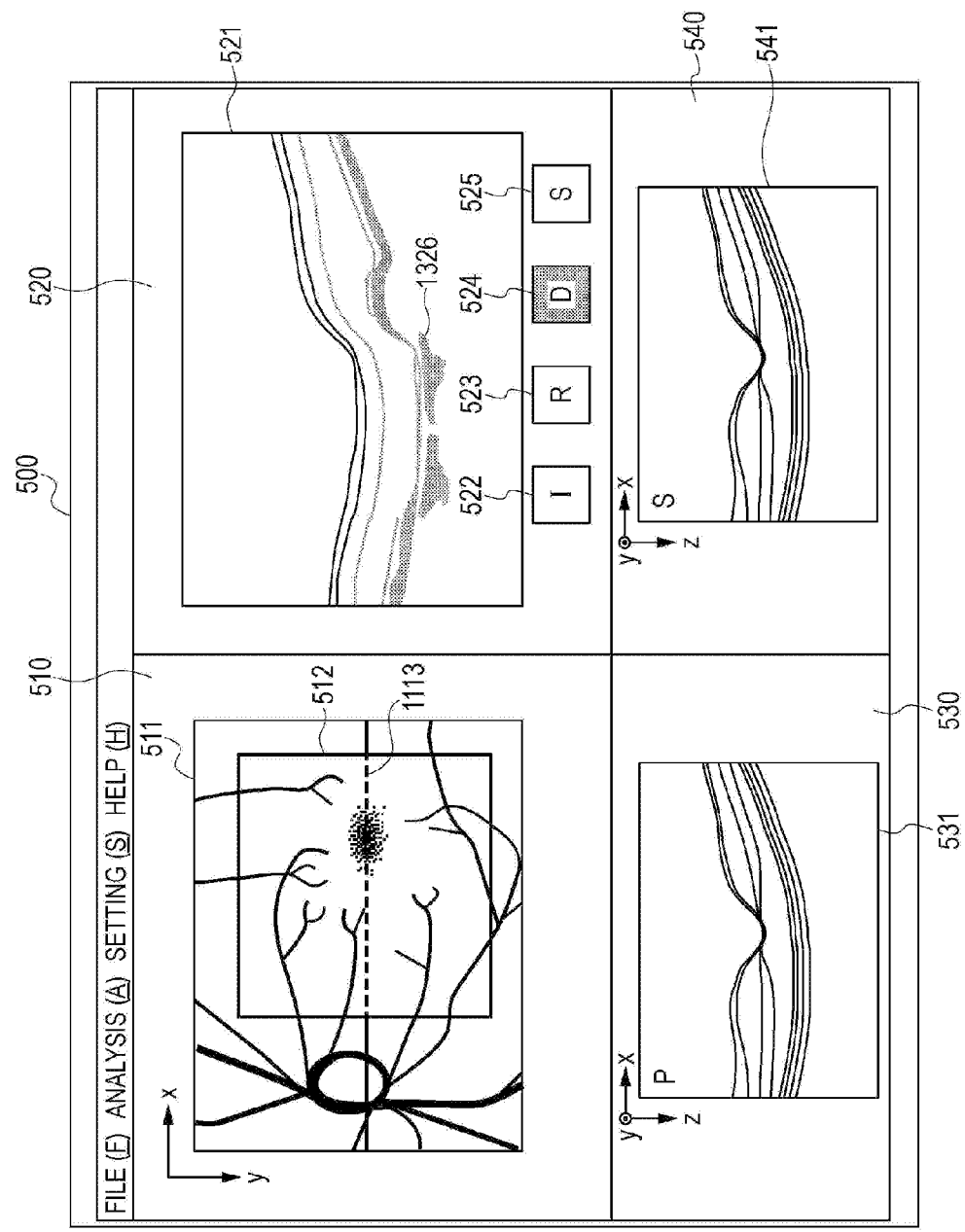

IMAGE PROCESSING APPARATUS AND IMAGE PROCESSING METHOD

BACKGROUND OF THE INVENTION

1. Field of the Invention

The present invention relates to an image processing apparatus and an image processing method for processing an image of a subject.

2. Description of the Related Art

An optical coherence tomography (hereinafter, referred to as OCT) in which multi-wavelength interference is employed can provide a high-resolution tomographic image of a sample (especially, an eye fundus).

In recent years, on an ophthalmologic OCT device, a polarization OCT image that images by using a polarization parameter (retardation and orientation), which is one of optical characteristics of the eye fundus tissue, is acquired in addition to an ordinary OCT image that images a shape of an eye fundus tissue.

In polarization OCT, a polarization OCT image is formed by using the polarization parameter, and differentiation and segmentation of the eye fundus tissue can be performed. In the polarization OCT, the polarization OCT image is generated by using a light, which is modulated into circular polarization, as a measuring light for observing the sample, and by dividing and detecting an interfering light as two linear polarization lights orthogonal to each other (see WO2010/122118A1). Note, however, that in the above-described literature, nothing is disclosed about a diagnostic assistance and, more specifically, about an ease of reading an eye fundus image and an ease of comparing images, which are an original object of the polarization OCT.

SUMMARY OF THE INVENTION

An object of the present invention is to display an image showing a polarization state on a display unit such that a user can effectively check such image. An image processing apparatus according to an embodiment of the present invention includes:

a planar image acquisition unit configured to acquire a planar image showing a polarization state of a subject;

a tomographic image acquisition unit configured to acquire a three-dimensional tomographic image including a plurality of two-dimensional tomographic images of the subject;

a display control unit configured to display, on a display unit, an index indicating a position of a tomographic image to be displayed on the display unit among the plurality of two-dimensional tomographic images, such that it is superimposed on the planar image showing the polarization state; and an instruction unit configured to give an instruction to change a position of the index on a planar image showing the polarization state. According to an embodiment of the present invention, it is possible to display an image showing a polarization state on a display unit such that a user can effectively check such image.

Further features of the present invention will become apparent from the following description of exemplary embodiments (with reference to the attached drawings).

BRIEF DESCRIPTION OF THE DRAWINGS

FIG. 13 is an exemplary display in the display area of the display unit of the image processing apparatus according to this embodiment.

DESCRIPTION OF THE EMBODIMENTS

An imaging apparatus according to an embodiment of the present invention is applicable to a subject such as an eye, a skin, and an internal organ to be examined. Furthermore, the imaging apparatus according to the embodiment of the present invention is, for example, an ophthalmologic apparatus, an endoscope, and the like. As an example of the embodiment of the present invention, the ophthalmologic apparatus according to this embodiment is described herein in detail with reference to the drawings.

[Overall Configuration of Device]

Figure 1:
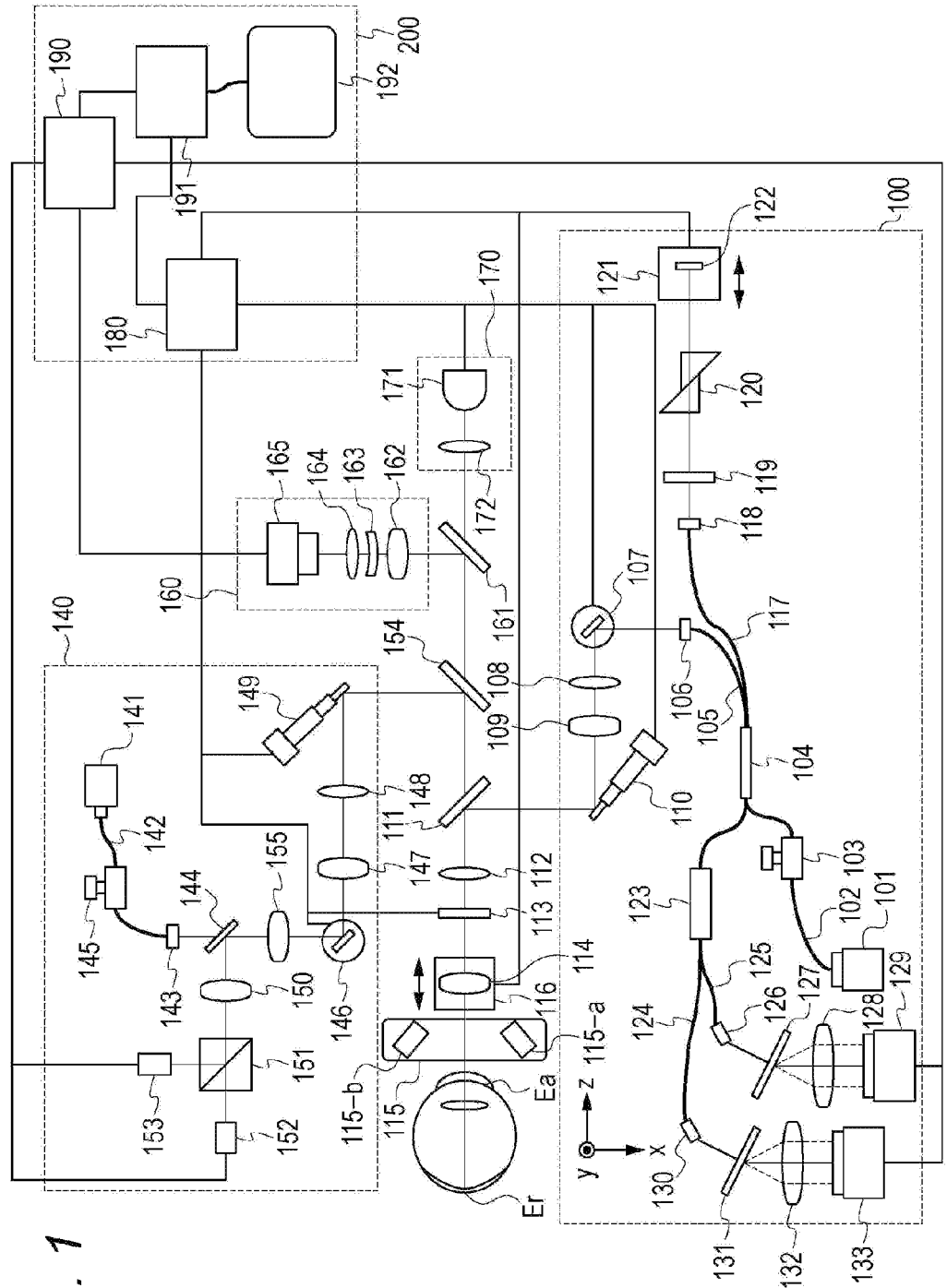
FIG. 1 is a schematic view of an overall configuration of an image processing apparatus according to this embodiment.

FIG. 1 is a schematic view of an overall configuration of an "ophthalmologic apparatus", which is an exemplary imaging apparatus according to this embodiment. Note that at least a part of a signal processing unit 190 described below can be regarded as an "image processing apparatus". In this case, the overall "ophthalmologic apparatus" can be regarded as an "ophthalmologic system" or the overall "imaging apparatus" can be regarded as an "imaging system".

This device includes a polarization sensitive OCT (hereinafter, referred to as PS-OCT) 100, a polarization sensitive scanning laser ophthalmoscope (hereinafter, referred to as PS-SLO) 140 in which polarization is employed, an anterior eye imaging unit 160, an inner fixation lamp 170, and a control unit 200.

An alignment of the device is performed in a state where the inner fixation lamp 170 is lightened up and gazes on an eye to be examined by using an image of an anterior eye of a subject observed by the anterior eye imaging unit 160. After the alignment has been completed, image capturing of the eye fundus is performed by the PS-OCT 100 and the PS-SLO 140.

<Configuration of PS-OCT 100>

A configuration of the PS-OCT 100 is described herein.

A light source 101 is a super luminescent diode (SLD) light source, which is a low coherent light source, and emits a light having a center wavelength of 850 nm and a bandwidth of 50 nm, for example. Although the SLD is used as the light source 101, any light source capable of emitting a low coherent light may be used such as an amplified spontaneous emission (ASE) light source.

The light emitted from the light source 101 is led to a fiber coupler 104, having a polarization maintaining function, through a polarization maintaining (PM) fiber 102 and a polarization controller 103, and is split into a measuring light (hereinafter, also referred to as "measuring light for a tomographic image" and "OCT measuring light") and a reference light corresponding to the measuring light.

The polarization controller 103 adjusts a state of polarization of the light emitted from the light source 101 to be a linear polarization light. The fiber coupler 104 has a branching ratio of 90 (reference light):10 (measuring light).

The measuring light is emitted from a collimator 106 through a PM fiber 105 as a parallel light. The emitted measuring light reaches a dichroic mirror 111 through an X scanner 107, which includes a galvanometer mirror for scanning an eye fundus Er with the measuring light in a horizontal direction, lenses 108 and 109, and a Y scanner 110, which includes a galvanometer mirror for scanning the eye fundus Er with the measuring light in a vertical direction. The X scanner 107 and the Y scanner 110 are controlled by a drive control unit 180, and are capable of scanning a desired range of the eye fundus Er with the measuring light. Note that the range of the eye fundus scanned with the measuring light can be regarded as an acquisition range of a tomographic image, an acquisition position of the tomographic image, or a radiation position of a measuring light. Furthermore, the X scanner 107 and the Y scanner 110 are examples of a scanning unit for the PS-OCT, and may also be configured as a common XY scanner. The dichroic mirror 111 has a property that a light between 800 nm and 900 nm is reflected and any other light is transmitted.

The measuring light reflected by the dichroic mirror 111, through a lens 112, becomes out of phase by 90 degrees by passing through a λ/4 polarizing plate 113, which is installed at a tilt of 45 degrees from p polarization to s polarization using an optical axis as a rotation axis, and is controlled to be a circular polarized light. Note that the λ/4 polarizing plate 113 is an example of a polarization adjustment member for the measuring light for adjusting a polarization state of the measuring light. Here, in a case where a below-described PS-SLO optical system is applied, the λ/4 polarizing plate 113 can be provided in a common optical path of a part of a PS-OCT optical system and a part of the PS-SLO optical system. Accordingly, it is possible to relatively restrain a variation in the polarization state that occurs between an image acquired by the PS-OCT optical system and an image acquired by the PS-SLO optical system. At this time, a scanning unit for the PS-SLO and a scanning unit for the PS-OCT are provided in a conjugate position with each other, and they can be provided in a conjugate position with a pupil of the eye to be examined. Note that a tilt of the λ/4 polarizing plate 113 is an example of a state of the λ/4 polarizing plate 113, and is, for example, an angle from a predetermined position where an optical axis of a polarization splitting surface of a fiber coupler 123, incorporating a polarization beam splitter, is used as the rotation axis.

Furthermore, the λ/4 polarizing plate 113 can be configured to be insertable and removable relative to the optical path. For example, a mechanical configuration may be possible in which the λ/4 polarizing plate 113 is rotated around by using the optical axis or an axis parallel to the optical axis as a rotation axis. Accordingly, it is possible to realize a small device capable of easily switching between an SLO optical system and the PS-SLO optical system. Furthermore, it is possible to realize a small device capable of easily switching between an OCT optical system and the PS-OCT optical system.

Here, a light entering an eye to be examined is controlled to be a circular polarized light by installing the λ/4 polarizing plate at a tilt of 45 degrees; however, depending on a characteristic of the eye to be examined, the light is not circular polarized at the eye fundus Er in some cases. Therefore, a tilt of the λ/4 polarizing plate is configured to be fine-adjustable by control of the drive control unit 180.

The measuring light controlled to be circular polarized is focused on a retina layer of the eye fundus Er by a focus lens 114 disposed on a stage 116 through an anterior eye Ea of an eye, which is the subject. The measuring light, which has irradiated the eye fundus Er, is reflected and scattered at each retina layer, and is returned to the fiber coupler 104 through the above-described optical path.

On the other hand, a reference light split at the fiber coupler 104 is emitted as a parallel light from a collimator 118 through a PM fiber 117. In the same way as the measuring light, the emitted reference light is controlled by a λ/4 polarizing plate 119, which is installed at a tilt of 22.5 degrees from p polarization to polarization using an optical axis as a rotation axis. Note that the λ/4 polarizing plate 119 is an example of a polarization adjustment member for the reference light for adjusting a polarization state of the reference light. The reference light is reflected by a mirror 122 on a coherence gate stage 121 through a dispersion compensation glass 120, and is returned to the fiber coupler 104. By passing through the λ/4 polarizing plate 119 twice, the reference light is returned to the fiber coupler 104 as a linear polarized light.

The coherence gate stage 121 is controlled by the drive control unit 180 to deal with a difference in an axial length of an eye of a subject and the like. Note that a coherence gate is a position corresponding to an optical path length of the reference light in an optical path of the measuring light. In this embodiment, the optical path length of the reference light is changed; however, any method may be used as long as a difference in the optical path length between the optical path of the measuring light and the optical path of the reference light can be changed.

A return light returned to the fiber coupler 104 and the reference light are combined to become an interference light (hereinafter, also referred to as combined light), which enters the fiber coupler 123 incorporating the polarization beam splitter, and is split into a p polarization light and an s polarization light, which are lights having different polarization directions, in a branching ratio of 50:50.

The p polarization light is dispersed by a grating 131 through a PM fiber 124 and a collimator 130, and is received by a lens 132 and a line camera 133. Similarly, the s polarization light is dispersed by a grating 127 through a PM fiber 125 and a collimator 126, and is received by a lens 128 and a line camera 129. Note that the gratings 127 and 131 as well as the line cameras 129 and 133 are disposed according to each polarization direction.

The light received by each of the line cameras 129 and 133 is output as an electric signal according to a strength of the light, and is received by the signal processing unit 190, which is an example of a tomographic image generating unit.

With respect to the tilt of the λ/4 polarizing plates 113 and 119, it is possible to automatically adjust it based on the tilt of the polarization splitting surface of the polarization beam splitter, but it may also be automatically adjusted relative to a straight line connecting an optic disk center and a macula center of the eye fundus. At this time, it is preferable that a tilt detecting unit (not illustrated) for detecting the tilt of the λ/4 polarizing plates 113 and 119 be provided. By this tilt detecting unit, it is possible to detect a current tilt and an achievement of a predetermined tilt. Of course, it is also possible to detect a degree of the tilt of the λ/4 polarizing plates 113 and 119 based on strength of the received light and adjust the tilt such that a predetermined strength is achieved. Note that, as described below, it is also possible to display an object showing the tilt on a GUI, and allow a user to adjust it by using a mouse. Furthermore, the same effect can be obtained by using a vertical direction as a polarization standard and by adjusting the polarization beam splitter and the λ/4 polarizing plates 113 and 119.

<Configuration of PS-SLO 140>

A configuration of the PS-SLO 140 is described herein.

A light source 141 is a semiconductor laser and emits a light having a center wavelength of 780 nm, for example, in this example. The measuring light emitted from the light source 141 (hereinafter, referred to as "measuring light for an eye fundus image" or "SLO measuring light"), goes through a PM fiber 142, is controlled to be linear polarized at a polarization controller 145, and is emitted as a parallel light from a collimator 143. The emitted measuring light passes through a perforated part of a perforated mirror 144, goes through a lens 155, goes through an X scanner 146 including a galvanometer mirror, which scans the eye fundus Er with the measuring light in a horizontal direction, lenses 147 and 148, and a Y scanner 149 including a galvanometer mirror, which scans the eye fundus Er with the measuring light in a vertical direction, and reaches the dichroic mirror 154. The X scanner 146 and the Y scanner 149 are controlled by the drive control unit 180, and are capable of scanning the eye fundus in a desired range with the measuring light. Note that the X scanner 146 and the Y scanner 149 are examples of a scanning unit for the PS-SLO, and may also be configured as a common XY scanner. The dichroic mirror 154 has a property that a light between 760 nm and 800 nm is reflected and any other light is transmitted.

The measuring light of linear polarization reflected by the dichroic mirror 154 goes through the same optical path as the PS-OCT 100 and reaches the eye fundus Er.

The measuring light, which has irradiated the eye fundus Er, is reflected and scattered at the eye fundus Er, follows the above-described optical path, and reaches the perforated mirror 144. The light reflected at the perforated mirror 144 goes through a lens 150, is split into a light having a different polarization direction (a p polarization light and an s polarization light in this embodiment) by a polarization beam splitter 151, is received at avalanche photodiodes (APD) 152 and 153, is converted into an electric signal, and is received at a signal processing unit 190, which is also an example of an eye fundus image generating unit.

Here, a position of the perforated mirror 144 is conjugate with a position of the pupil of the eye to be examined. Among the reflected and scattered light of the measuring light radiated to the eye fundus Er, the light that has passed through a peripheral area of a pupil is reflected by the perforated mirror 144.

In this example, the PM fiber is used for the PS-OCT and the PS-SLO, but the same configuration and the same effect can be obtained by using a single mode fiber (SMF) by controlling polarization using a polarization controller.

<Anterior Eye Imaging Unit 160>

An anterior eye imaging unit 160 is described herein.

The anterior eye imaging unit 160 radiates an anterior eye Ea by an illumination light source 115, which includes LEDs 115-a and 115-b emitting an illumination light having a wavelength of 1000 nm. The light reflected by the anterior eye Ea goes through the focus lens 114, the λ/4 polarizing plate 113, the lens 112, dichroic mirrors 111 and 154, and reaches a dichroic mirror 161. The dichroic mirror 161 has a property that a light between 980 nm and 1100 nm is reflected and any other light is transmitted. The light reflected by the dichroic mirror 161 goes through lenses 162, 163 and 164, and is received by an anterior eye camera 165. The light received by the anterior eye camera 165 is converted into an electric signal and is received by the signal processing unit 190.

<Inner Fixation Lamp 170>

An inner fixation lamp 170 is described herein.

The inner fixation lamp 170 includes a displaying unit 171 for the inner fixation lamp and a lens 172. As the displaying unit 171 for the inner fixation lamp, a plurality of light-emitting diodes (LDs) disposed in a matrix state is used. A position to light up the light-emitting diodes is changed according to a region to be captured an image by control of the drive control unit 180. A light from the displaying unit 171 for the inner fixation lamp is lead to the eye to be examined through the lens 172. The light emitted from the displaying unit 171 for the inner fixation lamp is 520 nm, and a desired pattern is displayed by the drive control unit 180.

<Control Unit 200>

A control unit 200 for controlling this device in general is described herein.

A control unit 200 includes the drive control unit 180, the signal processing unit 190, a display control unit 191, and a display unit 192.

The drive control unit 180 controls each unit as described above.

The signal processing unit 190, based on a signal output from each of the line cameras 129 and 133, the APDs 152 and 153, and the anterior eye camera 165, performs image generation, an analysis of the generated image, and generation of visualized information of an analysis result. Note that details of the image generation and the like are described below.

The display control unit 191 displays images, which are generated by a tomographic image generation unit and an eye fundus image generation unit, respectively, and acquired by an eye fundus image acquisition unit (not illustrated) and a tomographic image acquisition unit (not illustrated), and the like in a display area of the display unit 192. Here, the display unit 192 is, for example, a display such as of liquid crystal. Note that image data generated by the signal processing unit 190 may be transmitted to the display control unit 191 by wire or wirelessly. In this case, the display control unit 191 may be regarded as an image processing apparatus. Note that, as an imaging system, the eye fundus image acquisition unit may be configured to include the SLO optical system, and the tomographic image acquisition unit may be configured to include the OCT optical system. Herein, note that in a case where the subject is other than an eye to be examined, the "eye fundus image (eye fundus brightness image)" may also be referred to as a "planar image (planer brightness image)", and the "eye fundus image acquisition unit" may also be referred to as a "planar image acquisition unit".

The display unit 192 displays a display form showing different information under the control of the display control unit 191, as described below. Note that the image data from the display control unit 191 may be transmitted to the display unit 192 by wire or wirelessly. Furthermore, the display unit 192 and the like are included in the control unit 200; however, the present invention is not limited to this, and the display unit 192 and the like may be provided separately from the control unit 200. Furthermore, it may also be a tablet, which is an example of a device portable by a user, in which the display control unit 191 and the display unit 192 are integrally configured. In this case, it is preferable to install a touch panel function in the display unit and configure it such that operation such as moving of an image display position, an enlargement and a reduction, and a change of displayed image is possible on the touch panel.

[Image Processing]

Next, image generation and image analysis by the signal processing unit 190 is described herein. The signal processing unit 190 generates two tomographic images, which are a tomographic image corresponding to a first polarization and a tomographic image corresponding to a second polarization, based on each polarization component by performing a reconstruction processing used in a general spectral domain OCT (SD-OCT) on each of interference signals output from the line cameras 129 and 133.

First, the signal processing unit 190 performs a removal of a fixed pattern noise from the interference signal. The removal of the fixed pattern noise is performed by extracting the fixed pattern noise by averaging a plurality of detected A scan signals, and by subtracting this from an interference signal that has been input.

Next, the signal processing unit 190 converts the interference signal from a wavelength into a wavenumber and generates a tomographic signal showing a polarization state by performing a Fourier transformation.

Two tomographic images are generated by performing the above processing on the interference signals of two polarization components.

Furthermore, by synchronizing and aligning the signal output from the APDs 152 and 153 with drives of the X scanner 146 and the Y scanner 149, the signal processing unit 190 generates two eye fundus images based on each polarization component, which are an eye fundus image corresponding to the first polarization and an eye fundus image corresponding to the second polarization.

<Generation of Tomographic Brightness Image or Eye Fundus Brightness Image>

The signal processing unit 190 generates a tomographic brightness image from the above-described two tomographic signals.

The tomographic brightness image is basically the same as a tomographic image of a conventional OCT, and a pixel value r thereof is calculated by Formula 1 using tomographic signals $A_H$ and $A_V$ obtained by each of the line cameras 129 and 133.

[Formula 1]

$$r = \sqrt{A_H^2 + A_V^2} \qquad \text{Formula 1}$$

Similarly, an eye fundus brightness image is generated from two eye fundus images.

Figure 2B:
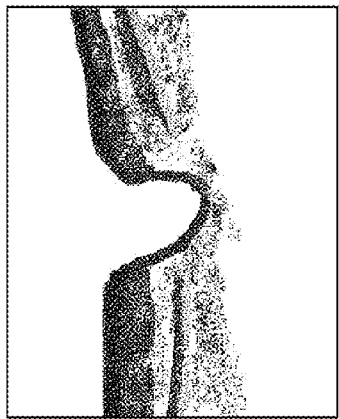
FIGS. 2A to 2E are exemplary images generated in a signal processing unit.
Figure 2A:
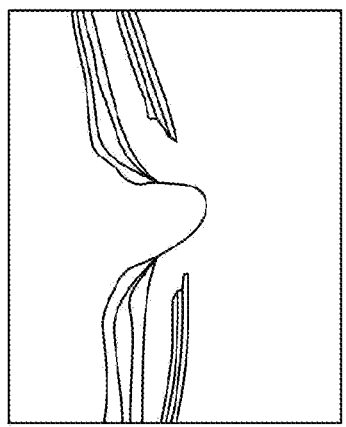

FIG. 2A is an exemplary brightness image of an optic disk part.

Note that when the λ/4 polarizing plate 113 is removed from the optical path, the display control unit 191 may display a tomographic brightness image acquired by a conventional OCT method on the display unit 192 or may display an eye fundus brightness image acquired by a conventional SLO method on the display unit 192.

<Generation of Retardation Image>

The signal processing unit 190 generates a retardation image from tomographic images of polarization components orthogonal to each other.

A value δ of each pixel of the retardation image is a value that shows a rate of an influence received by a vertical polarization component and a horizontal polarization component at an eye to be examined in a position of each pixel constituting a tomographic image, and is calculated by Formula 2 from each of the tomographic signals $A_H$ and $A_V$.

[Formula 2]

$$\delta = \arctan\left[\frac{A_V}{A_H}\right] \qquad \text{Formula 2}$$

FIG. 2B is an exemplary retardation image of the optic disk part generated in this way, which can be obtained by calculating Formula 2 for each B scan image. Here, as described above, the retardation image is the tomographic image showing a difference in the influence received by two polarizations at the eye to be examined. In FIG. 2B, a value showing the above-described rate is displayed as a tomographic image in full color. An area with a heavy gradation indicates that the value showing the above-described rate is small, while an area with a light gradation indicates that the value showing the above-described rate is large. Therefore, by generating the retardation image, it becomes possible to grasp a layer having birefringence. Note that details are as described in "E. Gotzinger et al., Opt. Express 13, 10217, 2005".

Similarly, the signal processing unit 190 can also generate a retardation image of the eye fundus in a planar direction based on an output from the APDs 152 and 153.

<Generation of Retardation Map>

The signal processing unit 190 generates a retardation map from a retardation image obtained for a plurality of B scan images.

First, the signal processing unit 190 detects a retinal pigment epithelium (hereinafter, referred to as RPE) in each of the B scan images. Since the RPE has a nature to resolve the polarization, for each A scan, a distribution of the retardation is studied in a range from an inner limiting membrane (hereinafter, referred to as "ILM") along a depth direction excluding the RPE, and a maximum value serves as a representative value of the retardation of the A scan.

The signal processing unit 190 generates a retardation map by performing the above processing on all of the retardation images.

Figure 2E:
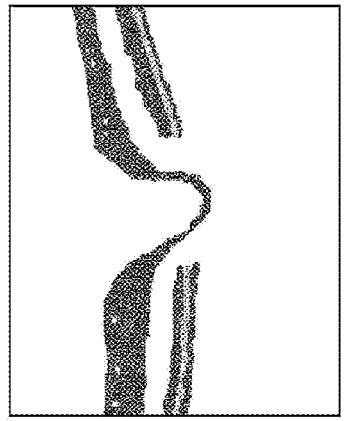
Figure 2D:
Figure 2C:
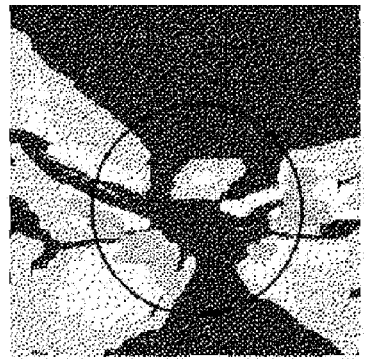

FIG. 2C is an exemplary retardation map of the optic disk part. An area with a heavy gradation indicates that the value showing the above-described rate is small, while an area with a light gradation indicates that the value showing the above-described rate is large. In the optic disk part, a nerve fiber layer retina (hereinafter, referred to as RNFL) is a layer having birefringence, and the retardation map shows a value indicating the above-described rate caused by the birefringence of the RNFL and the thickness of the RNFL. Therefore, in an area where the RNFL is thick, a value indicating the above-described rate becomes large, while in an area where the RNFL is thin, a value indicating the above-described rate becomes small. Therefore, it is possible to grasp the thickness of the RNFL of the entire eye fundus by the retardation map, whereby it can be used for a diagnosis of glaucoma.

<Generation of Birefringence Map>

The signal processing unit 190, in each of the A scan images of a retardation image generated in advance, performs a linear approximation of a value of the retardation δ in the range from the ILM to the RNFL, and determines the tilt as the birefringence of the A scan image in a position on the retina. That is, since the retardation is a product of a distance and the birefringence of the RNFL, a linear relation is obtained when values of depth and the retardation in each A scan image are plotted. Therefore, by performing the linear approximation of this plotting by a method of least squares and the like, and by obtaining a tilt thereof, a value of the birefringence of the RNFL in the A scan image is obtained. A map showing the birefringence is generated by performing this processing on all of the acquired retardation images.

FIG. 2D is an exemplary birefringence map of the optic disk part. Since in the birefringence map, a value of the birefringence is directly turned into a map, even if a thickness of the RNFL is not changed, if the fiber structure thereof is changed, it can be rendered as a change in the birefringence.

<Generation of DOPU Image>

The signal processing unit 190 calculates a Stokes vector S for each pixel by Formula 3 from the acquired tomographic signals $A_H$ and $A_V$, and a phase difference $\Delta\Phi$ therebetween.

[Formula 3]

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\Phi \\ 2A_H A_V \sin\Delta\Phi \end{pmatrix} \quad \text{Formula 3}$$

Note, however, that $\Delta\Phi$ is calculated as $\Delta\Phi = \Phi_V - \Phi_H$ from phases $\Phi_H$ and $\Phi_V$ of each signal obtained when calculating two tomographic images.

Next, the signal processing unit 190 sets a window, which is generally about 70 μm in a main scanning direction and about 18 μm in a depth direction of the measuring light for each B scan image, averages each factor of the Stokes vector calculated for each pixel by Number C within each window, and calculates a degree of polarization uniformity (DOPU), which is uniformity of polarization within the window, by Formula 4.

[Formula 4]

$$\text{DOPU} = \sqrt{Q_m^2 + U_m^2 + V_m^2} \quad \text{Formula 4}$$

Note, however, that $Q_m$, $U_m$ and $V_m$ are average values of Stokes vector factors Q, U and V within each window. By performing this processing on all windows within the B scan image, a DOPU image of the optic disk part in FIG. 2E is generated. Here, as described above, the DOPU image is a tomographic image that shows a degree of uniformity of two polarizations.

The DOPU is a numerical value indicating the uniformity of the polarization, and the DOPU becomes a numerical value close to one at a point where the polarization is maintained, and becomes a numerical value smaller than one at a point where the polarization is resolved and not maintained. In a structure within the retina, since the RPE has a nature to resolve the polarization state, a part corresponding to the RPE in the DOPU image has a value thereof smaller than the other areas. In the figure, a place having a light gradation indicates the RPE. Since the DOPU image images a layer that resolves the polarization such as of RPE, it is possible to certainly image the RPE even in a case where the RPE is deformed due to a disease and the like compared to a change in the brightness.

Similarly, the signal processing unit 190 can generate the DOPU image of the eye fundus in the planar direction based on outputs from the APDs 152 and 153.

Herein, note that the above-described tomographic images corresponding to the first and second polarizations, the retardation image, the DOPU image, and the like are also referred to as a tomographic image showing the polarization state. Furthermore, herein, the above-described retardation map, the birefringence map, and the like are also referred to as an eye fundus image showing the polarization state.

<Segmentation> the signal processing unit 190 performs segmentation of the tomographic image using the above-described brightness image.

First, the signal processing unit 190 applies a median filter as a type of smoothing and a Sobel filter as a type of edge detection to a tomographic image to be processed, and creates respective images (hereinafter, referred to as "median image" and "Sobel image"). Next, from the median image and the Sobel image that are created, a profile is created for each A scan. The profile is a brightness value profile for the median image and a gradient profile for the Sobel image. Then, a peak is detected within the profile created from the Sobel image. By referring to a profile of the median image corresponding to before and after the detected peak and between the peaks, a boundary of each area of the retina layer is extracted.

Furthermore, a thickness of each layer is measured in a direction of the A scan line, and a layer thickness map is created for each layer.

[Processing Operation]

Next, a processing operation of this image processing apparatus is described herein.

Figure 3:
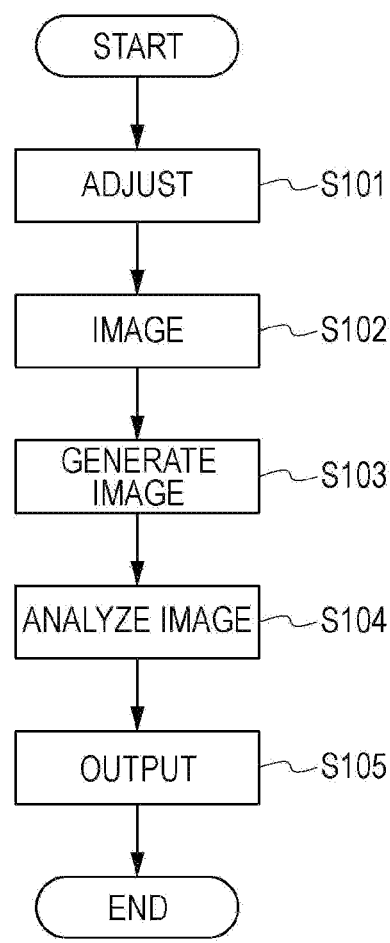
FIG. 3 is a processing flow according to this embodiment.

FIG. 3 is a flowchart illustrating the processing operation of this image processing apparatus.

<Adjustment>

First, in step S101, in a state where an eye to be examined is disposed in this device, an alignment is performed between the device and the eye to be examined. With respect to a description of the alignment, processing peculiar to this embodiment will be described herein, and an alignment in X, Y and Z directions of a working distance and the like, a focus, an adjustment of the coherence gate, and the like are general, whereby descriptions will be omitted.

(Adjustment of PS-OCT Imaging Position)

Figure 4:
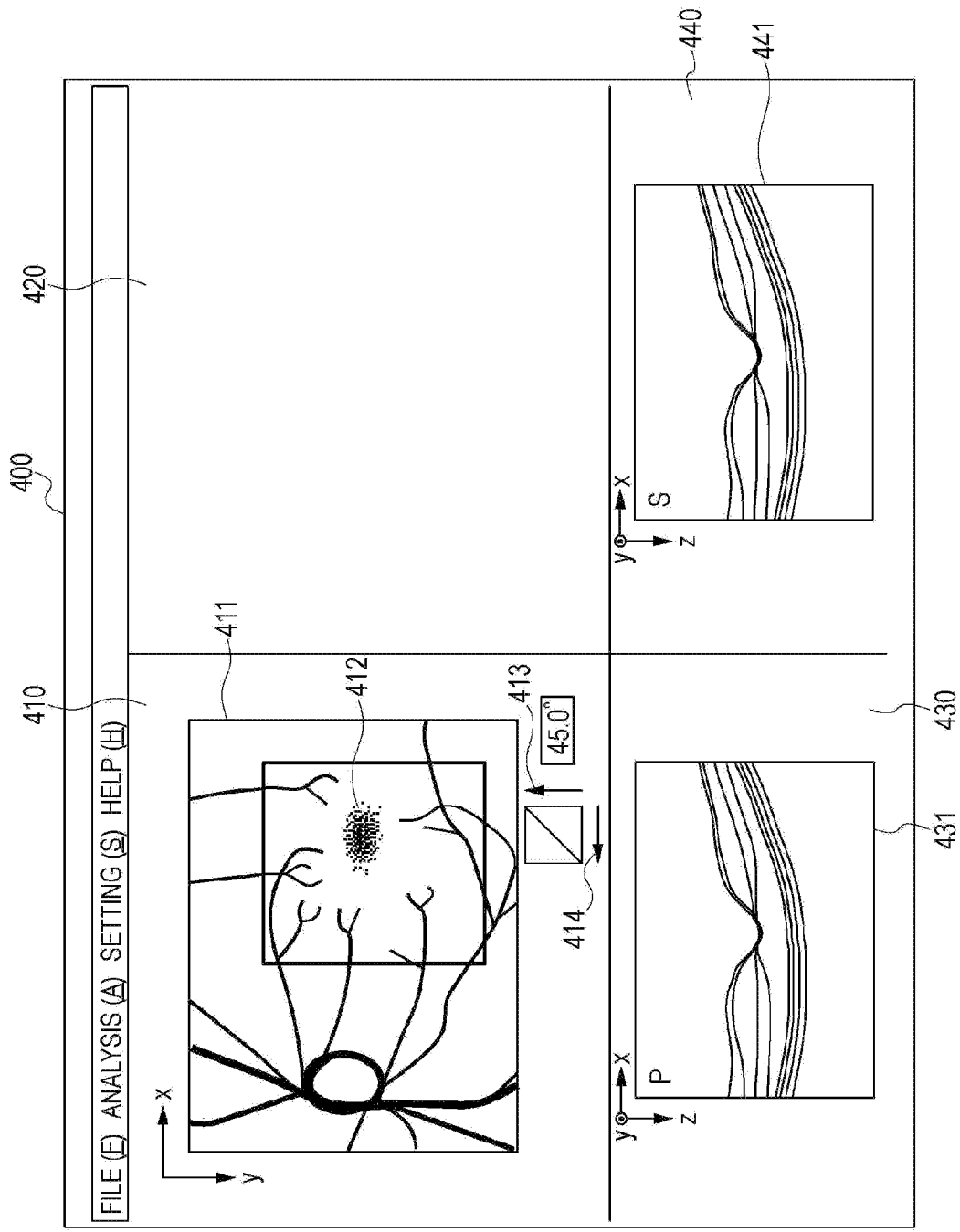
FIG. 4 is an exemplary display in a display area of a display unit of the image processing apparatus according to this embodiment.

FIG. 4 is a view of a window 400 displayed on the display unit 192 during adjustment. On a display area 410, which is an example of a first display area, an eye fundus image 411 imaged by the PS-SLO 140 and generated by the signal processing unit 190 is displayed, and on the eye fundus image 411, a frame 412 showing an imaging range of the PS-OCT 100 is superimposed.

By an operator specifying with a cursor displayed on the window 400 using an instruction device such as a mouse (not illustrated), and by instructing using a click operation, a drag operation, and the like, a setting of the imaging range is performed under the control of the drive control unit 180. That is, by specifying the frame 412 with the cursor and by performing the drag operation, it is possible to move the frame 412. Accordingly, the drive control unit 180 sets the imaging range by controlling a drive angle of a scanner. Note that the mouse according to this embodiment is provided with, for example, a sensor for detecting a movement signal when a main body of the mouse is two-dimensionally moved by a hand of a user, two mouse buttons in the right and in the left for detecting an pressing operation by the hand of the user, and a wheel mechanism, which can be rotated back and forth and to the right and to the left, disposed between the two mouse buttons in the right and the left. Furthermore, a touch panel function may be installed to the display unit of the instruction device, and an acquisition position may be specified on the touch panel.

(Adjustment of λ/4 Polarizing Plate)

Adjustment of the λ/4 polarizing plate 113 is described herein.

In FIG. 4, instruction units 413 and 414 are displays for adjusting an angle of the λ/4 polarizing plate 113. By an operator instructing using the instruction device, the angle of the λ/4 polarizing plate 113 is adjusted under the control of the drive control unit 180. The instruction unit 413 is a display for instructing an adjustment counterclockwise, and the instruction unit 414 is a display for instructing an adjustment clockwise. A numerical value displayed alongside the instruction units 413 and 414 indicates a current angle of the λ/4 polarizing plate 113. Note that the display control unit 191 may display the instruction unit for adjusting an angle of the λ/4 polarizing plate 119 on the display unit 192 next to the instruction unit 413 or may display it in place of the instruction unit 413.

The operator instructs with a cursor by using a mouse such that the brightness becomes the same between tomographic images of each polarization displayed on a display area 430, which is an example of a third display area, and a display area 440, which is an example of a fourth display area. Note that it is also possible to configure such that a peak brightness value is displayed or a waveform of each interference signal is directly displayed with tomographic images 431 and 441 of each polarization, and an adjustment is made while looking thereat. Here, the tomographic images 431 and 441 of each polarization are examples of a tomographic image corresponding to the first polarization and a tomographic image corresponding to the second polarization. Note that on the tomographic images 431 and 441 of each polarization (or the tomographic images 531 and 541 described below), it is preferable that a display form showing each image type, for example, a character "P" showing the p polarization and a character "S" showing the s polarization, be displayed being superimposed on the image. Accordingly, it is possible to prevent a user from falsely recognizing the image. Of course, it is also possible to display the display form on the top or the side of the image without displaying it by superimposing on the image, as long as it is displayed so as to correspond with the image.

Furthermore, in the display area 420, which is an example of a second display area, nothing may be displayed at this stage, or in a case of auto adjustment and the like, the display form indicating a current adjustment state, for example, a message such as "adjusting the λ/4 polarizing plate" may be displayed. Furthermore, a display form indicating patient information such as a right and left eye of the eye to be examined or a display form indicating imaging information such as an imaging mode may be displayed in the window 400. Note that it is desirable that the λ/4 polarizing plate 113 be inserted to and removed from the optical path repeatedly such that the eye fundus brightness image and the tomographic image showing the polarization state are acquired alternately. Accordingly, the display control unit 191 can, for example, display the eye fundus brightness image in the display area 410 and the tomographic image showing the polarization state in the display area 420 in an ophthalmologic apparatus as small as possible.

Here, with regard to an order of adjustment, it is preferable that the order be an alignment adjustment using an anterior eye image and a cornea bright spot, a focus adjustment using the eye fundus image showing the polarization state, a coherence gate adjustment using the tomographic image showing the polarization state, and an adjustment of the λ/4 polarizing plate. Note that it is preferable that a determination of an acquisition position of the tomographic image showing the polarization state be before an adjustment of the coherence gate using the tomographic image showing the polarization state; however, it is also possible to determine the acquisition position in the initial setting so as to acquire a center area of the eye fundus image showing the polarization state. Accordingly, it is possible to make an easy adjustment such that the tomographic image showing the polarization state, which deals with a finer and narrower range than the eye fundus image showing the polarization state, can be acquired accurately. At this time, the λ/4 polarizing plate may be automatically adjusted according to completion of the coherence gate adjustment, or the λ/4 polarizing plate may be automatically adjusted according to an input of a signal for acquiring an image showing the polarization state. Of course, it is also possible to configure such that the λ/4 polarizing plate is adjusted in advance in an initial setting screen or the like when the ophthalmologic apparatus is started up, such that no adjustment is performed for each imaging.

Furthermore, in a case where the λ/4 polarizing plate is configured to be insertable and removable relative to the optical path, it is preferable that the order of an adjustment be in the order of, an alignment adjustment using the anterior eye image and the cornea bright spot, a focus adjustment using the SLO eye fundus image, a coherence gate adjustment using the OCT tomographic image, insertion of the λ/4 polarizing plate into the optical path, and an adjustment of the λ/4 polarizing plate. Accordingly, an adjustment prior to acquiring of an image showing the polarization state can be performed using an ordinary SLO eye fundus image and an OCT tomographic image, with which the user is intuitively familiar. Note, however, it is also possible to perform the coherence gate adjustment using the tomographic image showing the polarization state of the PS-OCT after the focus adjustment, after the λ/4 polarizing plate is inserted. At this time, according to the completion of the coherence gate adjustment or the completion of the focus adjustment, the λ/4 polarizing plate may be automatically inserted into the optical path, or the λ/4 polarizing plate may be automatically inserted into the optical path according to the input of a signal for acquiring the image showing the polarization state.

Note that in the focus adjustment, it is also possible to perform a fine focus adjustment using the OCT tomographic image after a rough focus adjustment using the SLO eye fundus image has been performed.

Furthermore, these adjustments may be performed fully automatically in the above-described order, or may be performed by pointing a cursor to a slider corresponding to each adjustment displayed on the display unit for a dragging operation and the like. Furthermore, in a case where the λ/4 polarizing plate is inserted and removed, an icon may be displayed on the display unit for instructing the insertion of the λ/4 polarizing plate into the optical path or the removal thereof from the optical path.

<Imaging> to <Analyzing>

In Steps S102 to S104, a measuring light is emitted from each of the light source 101 and the light source 141, a return light from the eye fundus Er is received by the line cameras 129 and 133 and the APDs 152 and 153, and each image is generated and analyzed as described above in the signal processing unit 190.

<Output>

Next, Step S105, which is output processing of each of the generated images and analyzed results, is described herein.

Once generation and analysis of each image has been completed in the signal processing unit 190, based on the result, the display control unit 191 generates output information and outputs it to the display unit 192 for display.

Figure 5:
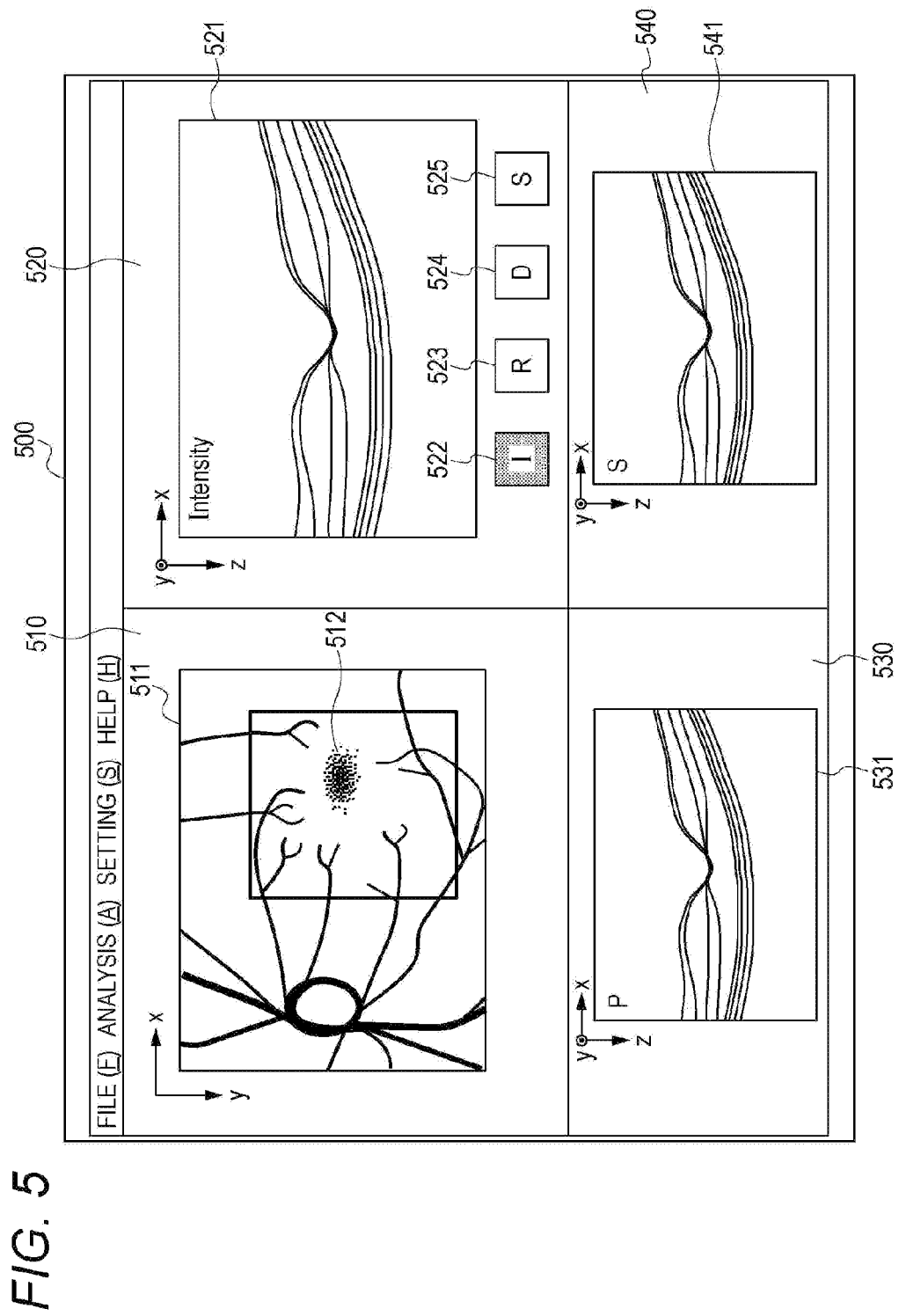
FIG. 5 is an exemplary display in the display area of the display unit of the image processing apparatus according to this embodiment.

FIG. 5 is an exemplary display on the display unit 192 according to this embodiment.

In the figure, a reference numeral 500 denotes a window displayed on the display unit 192, and a window 500 includes display areas 510, 520, 530 and 540.

In the display area 510, which is an example of the first display area, an eye fundus image 511 is displayed, and a rectangular frame 512 indicating a position of the tomographic image is superimposed thereon. As the eye fundus image 511, an eye fundus brightness image is displayed, which may also be an eye fundus image based on the polarization signal.

In the display area 520, which is an example of the second display area, a tomographic image 521 is displayed. Furthermore, in the display area 520, buttons 522 to 525 are displayed, which are examples of a selection unit for selecting a type of the tomographic image to be displayed. Note that it is also possible to select the type of the tomographic image from a menu instead of the buttons 522 to 525. In FIG. 5, a state in which the button 522 is selected is shown.

In a display area 530, which is an example of the third display area, and in a display area 540, which is an example of the fourth display area, respective tomographic images 531 and 541 based on each polarization signal for generating the tomographic image 521 are displayed. Note that the images displayed in the display areas 530 and 540 may also be respective eye fundus images based on each polarization signal that has generated the eye fundus image displayed in the display area 510 based on an instruction, for example, a selection from the menu, by the operator.

Note that on the tomographic brightness image 521, the retardation image 621 described below, the DOPU image 721, and the like, it is preferable that a display form showing each image type, for example, a text "Intensity", a text "Retardation", and a text "DOPU" be superimposed on the image for display. Accordingly, it is possible to prevent a user from falsely recognizing an image. Of course, it is also possible to display the display form on the top or the side of the image without displaying it by superimposing on the image, as long as it is displayed so as to correspond with the image.

Figure 6:
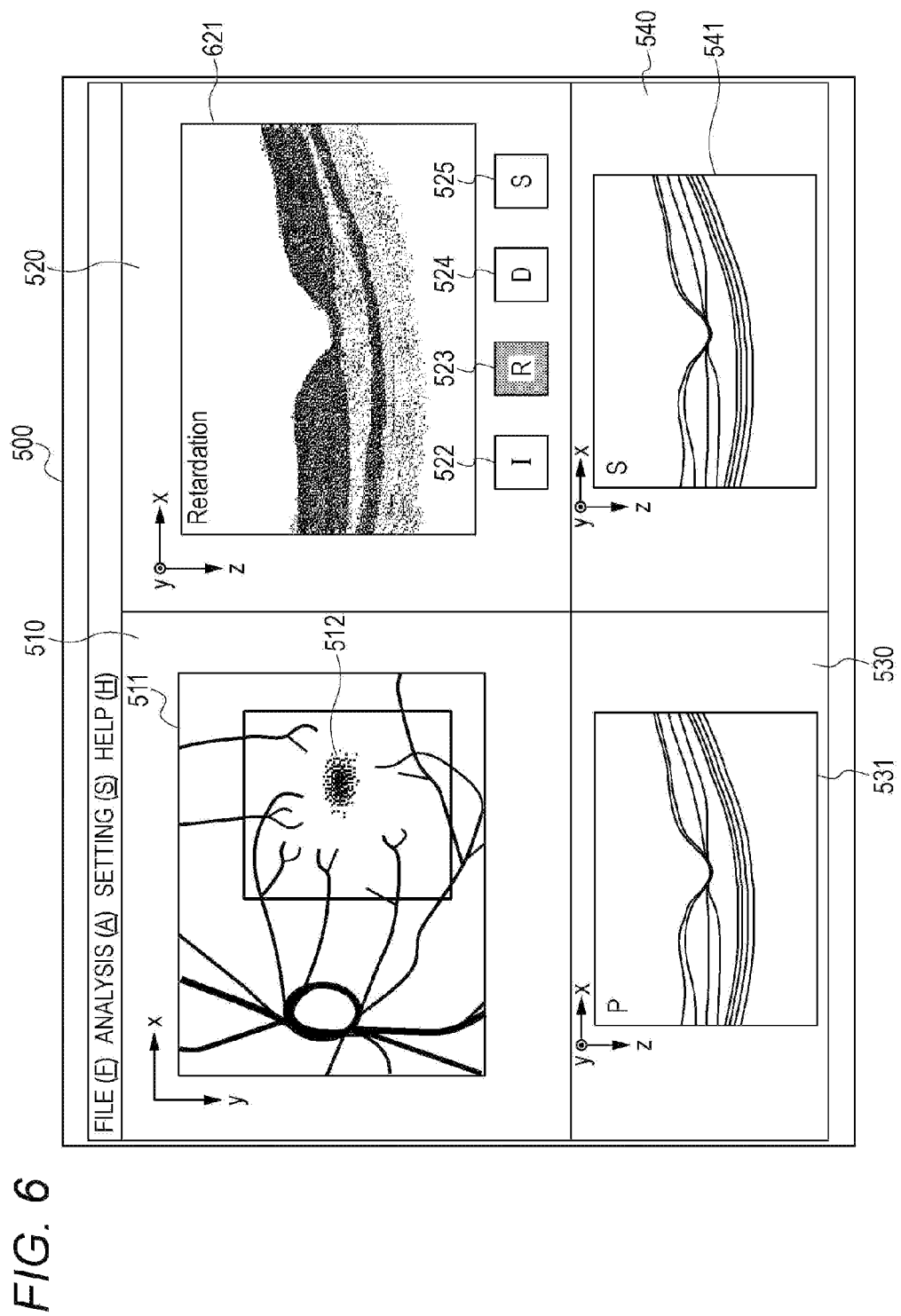
FIG. 6 is an exemplary display in the display area of the display unit of the image processing apparatus according to this embodiment.

As in FIG. 6, the tomographic image displayed in the display area 520 may be changed to a retardation image 621 by the operator instructing the button 523.

In the display areas 530 and 540, similar to FIG. 5, the tomographic images 531 and 541 are displayed.

Figure 7:
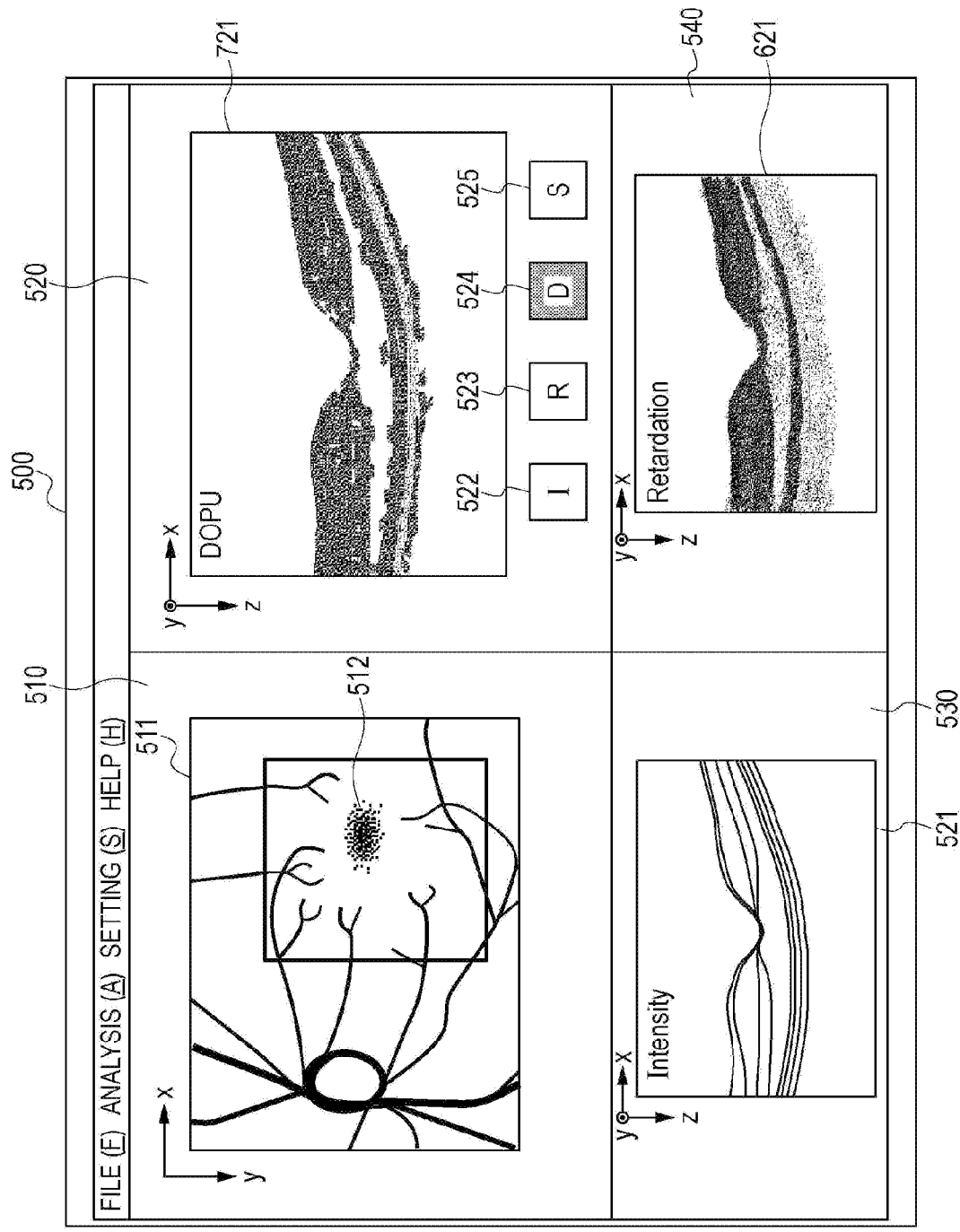
FIG. 7 is an exemplary display in the display area of the display unit of the image processing apparatus according to this embodiment.

As in FIG. 7, the tomographic image displayed in the display area 520 may be changed to a DOPU image 721 by the operator instructing the button 524.

In a display area 530, a brightness image 521 is displayed, and in a display area 540, a retardation image 621 is displayed. Here, it is preferable that a button be prepared such that an image can be selected for each display area. Accordingly, a user can easily select images to be compared, for example, a plurality of tomographic images each showing a different polarization state.

Figure 8:
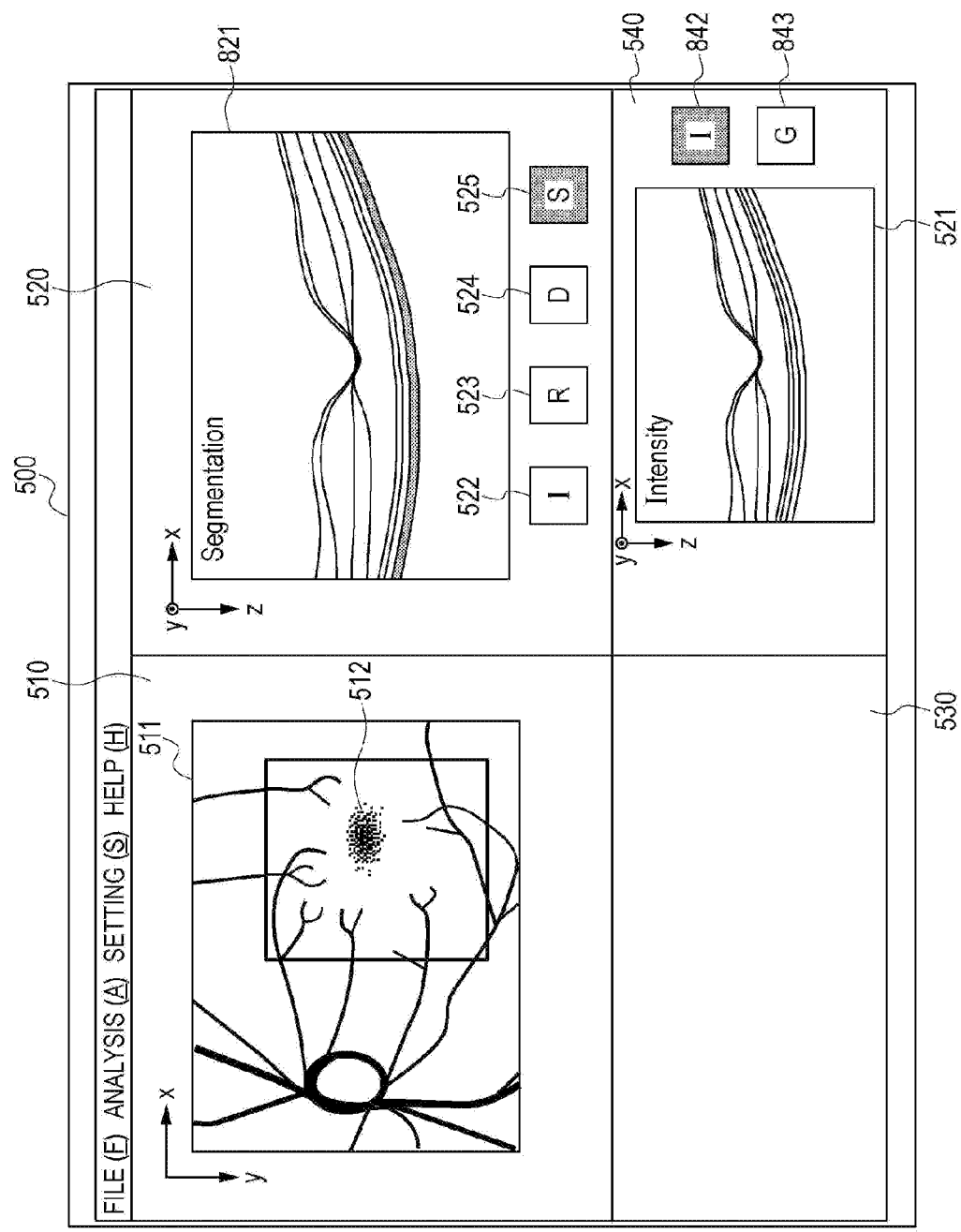
FIG. 8 is an exemplary display in the display area of the display unit of the image processing apparatus according to this embodiment.

By the operator instructing from the button 525, as in FIG. 8, the tomographic image displayed in the display area 520 can be changed to an image 821, which is a segmentation result. In the image 821, a colored line segment showing a layer boundary is superimposed on the tomographic image, and the RPE is highlighted. A layer selected by the operator using a cursor is highlighted.

In a display area 540, a tomographic brightness image 841 used in the segmentation and buttons 842 and 843 are displayed. By instructing from these buttons 842 and 843, it is possible to switch between the tomographic brightness image 841 and a graph 941 indicating a layer thickness of the highlighted layer (see FIG. 9).

Figure 9:
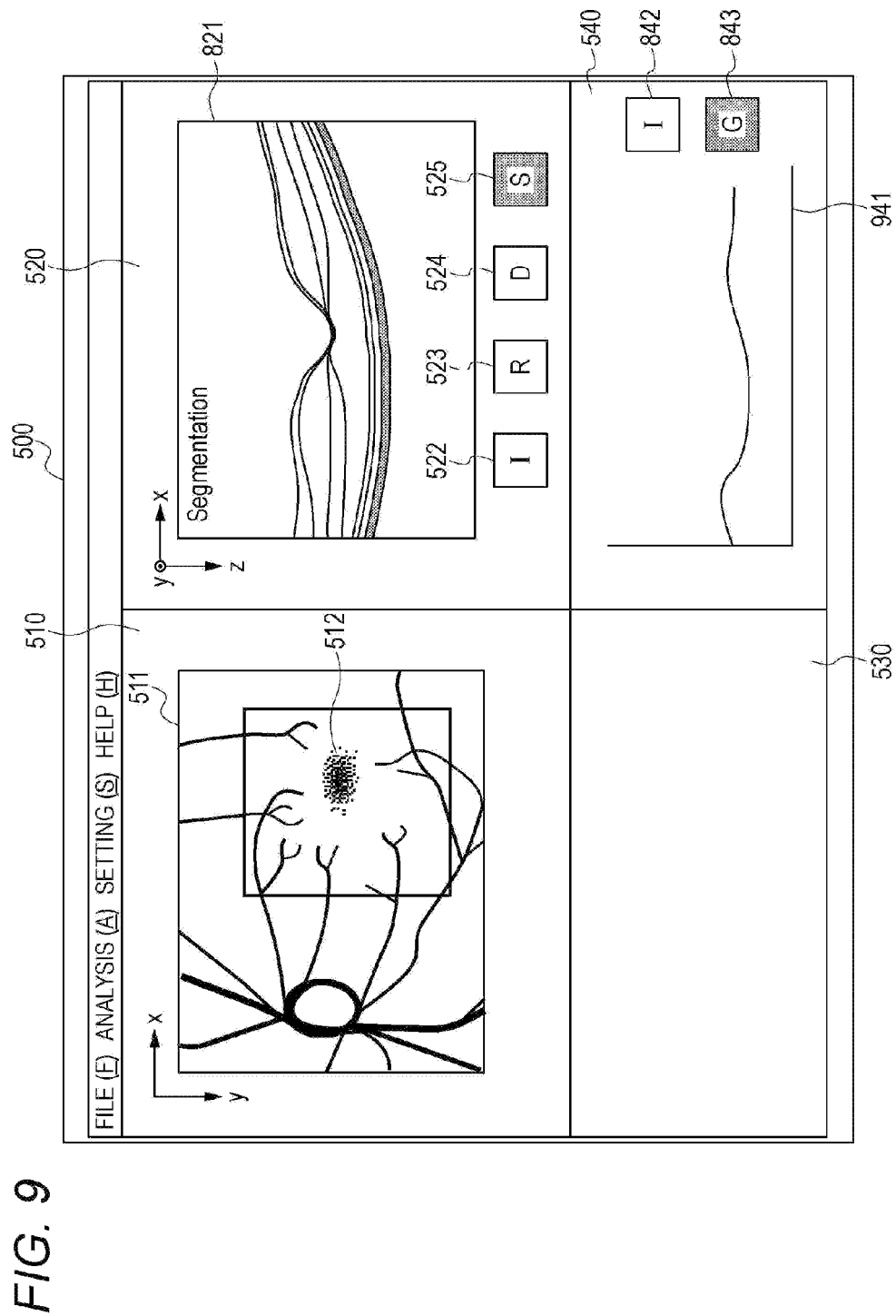
FIG. 9 is an exemplary display in the display area of the display unit of the image processing apparatus according to this embodiment.
Figure 10:
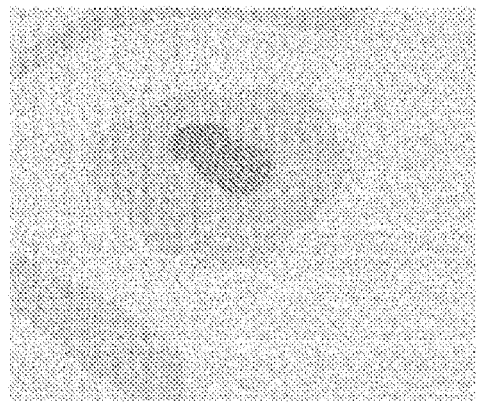
FIG. 10 is an exemplary two-dimensional layer thickness map displayed in the display unit of the image processing apparatus according to this embodiment.

Furthermore, in FIG. 9, thickness information of the selected layer (for example, two-dimensional layer thickness map shown in FIG. 10) may be displayed in a display area 530. In FIG. 10, the thickness of the selected layer is shown with a difference in color. Note that an integrated image may be displayed in place of the thickness of the selected layer shown in FIG. 10. Note that as the integrated image, it may be an integrated image based on a specific layer or the entire PS-OCT. Furthermore, a case where the displayed image is changed by the instruction of the operator has been described, but it is also possible to display an image, which is prioritized for a disease in advance, on each display area by selecting information of a disease to be diagnosed, for example, by selecting a name of the disease from a menu.

Note that the display control unit 191 may display a retardation map or a birefringence map in place of the above-described various images in any of each display area of the display unit 192. Furthermore, the display control unit 191 may display a retardation map or a birefringence map by superimposing it on the eye fundus brightness image 511. At this time, it is preferable that the retardation map or the birefringence map be displayed being superimposed on an area shown with a frame 512.

As described above, according to this embodiment, it is possible to efficiently present each of the generated images to the operator.

Furthermore, it is possible to select an image that the operator needs with a simple operation. Especially, the operation becomes further simpler by matching a disease name with a displayed image.

Furthermore, a polarization adjustment of the measuring light can be performed easily.

Note that a position of the display area to display these images is not limited to this embodiment, and may be displayed, for example, in a display area on the left side of the display screen of the eye fundus image. Furthermore, the number of the images to be displayed is not limited to this embodiment. For example, during adjustment, two images, which are the eye fundus image and the tomographic image, in total may be displayed side by side in the display area, and after imaging, a display method may be changed, and in addition to the eye fundus image, a plurality of tomographic images, each showing a different polarization state, may be displayed side by side in the display area. Furthermore, the order, the position, and the like of alignment of the buttons 522 to 525 are also not limited to this embodiment.

(Index Showing Position of Tomographic Image Showing Polarization State)

Figure 11:
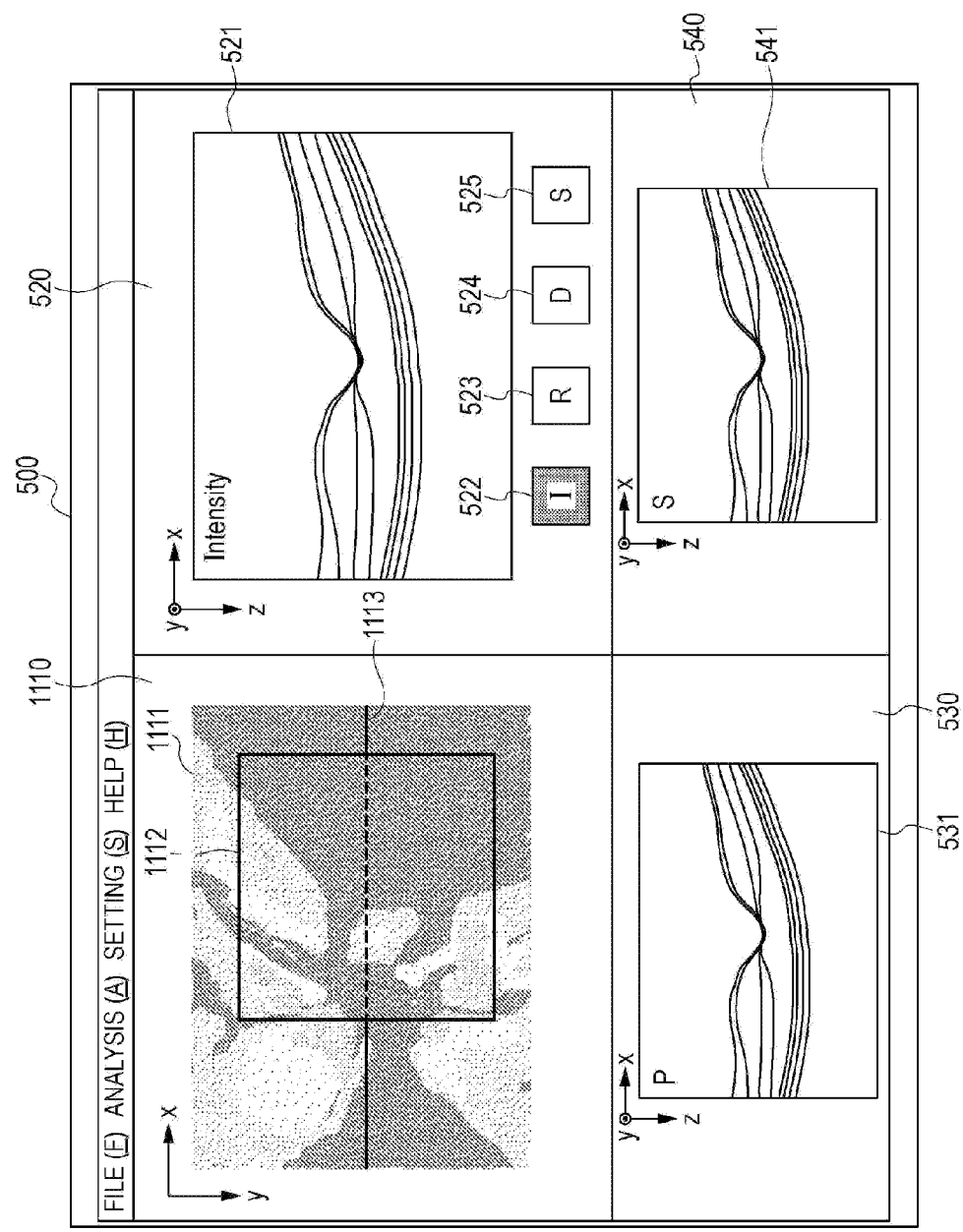
FIG. 11 is an exemplary display in the display area of the display unit of the image processing apparatus according to this embodiment.

Furthermore, as an index indicating a position of the tomographic image displayed on the display area 520 relative to the eye fundus image displayed in the display area 510, by superimposing a linear cursor, more effective image display can be performed. FIG. 11 is an exemplary display on the display unit 192 according to this embodiment, and a type of the window displayed on the display unit 192 is the same as that in the above-described example. In the display area 1110, a retardation map 1111 is displayed, and a rectangular frame 1112 showing the position of the tomographic image is superimposed thereon.

In the display area 520, a tomographic image (brightness image) 521 is displayed. A reference numeral 1113 denotes a tomographic position specification cursor, which shows a position of the tomographic image (brightness image) 521 displayed on the display area 520 and can be moved by an instruction from the display control unit 191 or by the operator using the instruction device such as a mouse. Note that this tomographic position specification cursor 1113, as in FIG. 11, may be displayed throughout the entire retardation map 1111 or only in a part displayed in the display area 520, which may be superimposed on the eye fundus image. Furthermore, in FIG. 11, the tomographic position specification cursor 1113 is displayed with a broken line in a range displayed in the display area 520 and with a solid line in any other area. Differentiation of this cursor is not limited to a change of line type, and it is also possible to change a color.

Furthermore, in a display area 520, the buttons 522 to 525 are displayed for selecting a type of the tomographic image to be displayed. Note that in place of the buttons 522 to 525, it is also possible to select the type of the tomographic image from the menu. FIG. 11 shows a state in which the button 522 is selected. In areas 530 and 540, the respective tomographic images 531 and 541 are displayed, which are based on each polarization signal used for generating a tomographic image (brightness image) 521.

By operating this tomographic position specification cursor 1113, it is possible to change the position of the tomographic image (brightness image) 521 on the retardation map displayed in the display area 520. While looking at the retardation map 1111 displayed in a display area 1110, the operator can move the tomographic position specification cursor 1113 to a desired position and can display the tomographic image of a position, which the operator wants to observe, in the display area 520. Note that it is also possible to configure such that the tomographic image displayed in the display area 520 is renewed along with a movement of the tomographic position specification cursor 1113, and based on an instruction from the operator, a desired tomographic image is fixedly displayed.

At this time, the tomographic image is not limited to a brightness image, and it may also be a retardation image or a DOPU image; however, in a case where the retardation map is displayed in the display area 1110, the brightness image is desirable, as the following effect may be obtained. That is, as described above, the retardation map is a value determined by both the birefringence and the thickness of the RNFL, but on the map, to know the thickness of the RNFL of an area where the retardation value is relatively smaller than other areas, it is necessary to directly observe the tomographic image (brightness image). At this time, it is preferable that the retardation value and the RNFL thickness corresponding to a position of the index be displayed on a monitor. Note that an area having a smaller retardation value may be an area where the value is smaller than a threshold value such as a normal value prepared in advance. Furthermore, it is also possible to display a display form showing that it is an area having a smaller value, superimposed on the retardation map.

Therefore, according to the method explained in this example, while obtaining a general overview on the retardation map, a state of the RNFL of an area where it is considered to be necessary to obtain a further detailed observation can be displayed more effectively. Note that an image displayed on the display area 1110 is not limited to the retardation map, but it may also be an eye fundus image 511 or a birefringence map described above as long as it is an image showing an eye fundus on an XY plane.

(Plurality of Indexes)

Furthermore, it is also possible to display a plurality of above-described tomographic position specification cursors.

Figure 12:
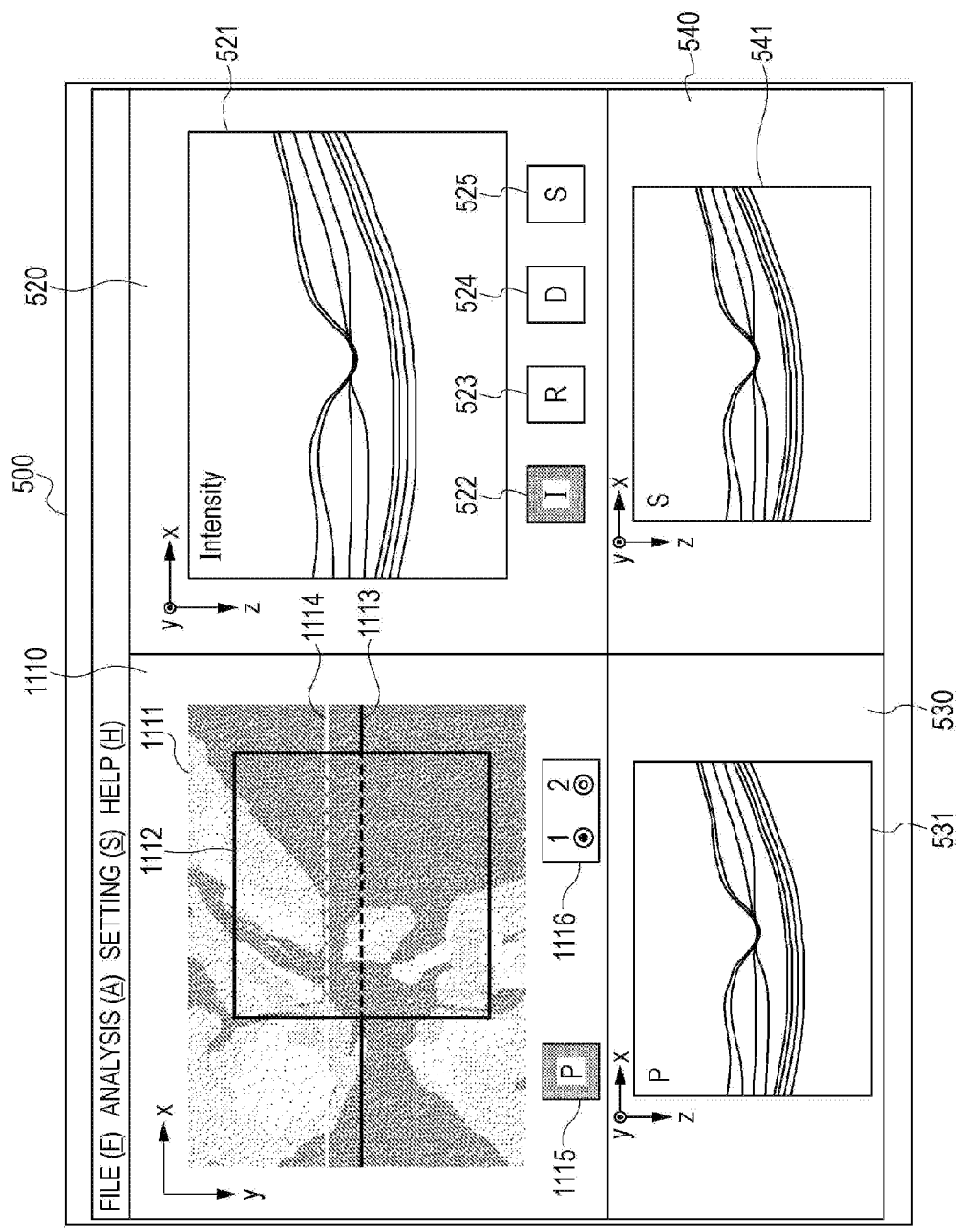
FIG. 12 is an exemplary display in the display area of the display unit of the image processing apparatus according to this embodiment.

FIG. 12 is a graphic illustration of such an example in which a first tomographic position specification cursor 1113, which is an example of a first index, and a second tomographic position specification cursor 1114, which is an example of a second index, are displayed. At this time, each cursor can be moved by an operator using an instruction device such as a mouse. Accordingly, a tomographic image for each position can be displayed on the display area 520. This is effective for a diagnosis because, for example, a user can compare tomographic images of multiple positions, which are effective for the diagnosis.

The plurality of tomographic position specification cursors 1113 and 1114 can be displayed by operating a cursor display switching button 1115. For example, it may be possible to configure such that, when a user presses the cursor display switching button 1115 by using a mouse or the like, one cursor is increased into one or more cursors, and when the user presses the cursor display switching button 1115 again, these cursors returns to a single cursor. Furthermore, in the case where there is a plurality of tomographic position specify cursors, a cursor to be displayed in the display area 520 may be specified by operating a display switching radio button 1116. In FIG. 12, by pressing a radio button denoted as 1, a tomographic image corresponding to the first tomographic position specification cursor is displayed on the display area 520. Furthermore, as in this example, in a case where there is a plurality of cursors, it is desirable that a color and a shape of a line thereof be displayed to be identifiable.

Furthermore, it is also possible to configure such that any one of the cursors is fixed as a standard cursor, which cannot be changed a position thereof, while the other is moveable by the operator. The cursor may be fixed, for example, by clicking a button on a mouse or by separately operating a cursor fix button not illustrated, on a fixed specification cursor. Accordingly, the other cursor can be moved to a position symmetric to a fixed standard cursor, for example, relative to a line passing through an optic disk and a macula. At this time, by a user comparing corresponding two tomographic images laid out in symmetric positions or by comparing the thickness of the RNFL, it is possible to effectively diagnose a glaucoma and the like.

Furthermore, by fixing one of the cursors and measuring a distance between the standard cursor and the moveable cursor, it is possible to obtain a distance between the tomographic images. Specifically, by the display control unit 191 calculating and displaying a distance between two cursors, it becomes possible for the operator to manually measure the distance on the retardation map. Since the retardation map changes with progression of the glaucoma, it is possible to measure the size of a part where a change is occurring (for example, an area having the retardation value relatively smaller than other areas in the retardation map). At this time, it is preferable that the display form showing the measured distance be displayed on the display unit. For example, it is preferable that the measured distance be displayed being superimposed on the eye fundus image showing the polarization state. Accordingly, it is possible to make a diagnosis effectively. Note that the same operation is possible in a case where the birefringence map is a target.

Furthermore, the display form of the tomographic image can take various forms other than the above-described exemplary method. For example, two tomographic images may be displayed side by side on a display area 520 by pressing the cursor display switching button 1115, or a tomographic image of respective cursor positions may be displayed on the display areas 530 and 540.

In this way, when two tomographic images are displayed simultaneously, a tomographic image corresponding to each of the tomographic position specification cursors 1113 and 1114 is displayed side by side while maintaining a positional relationship thereof. Furthermore, it is preferable to draw a display frame of each tomographic image according to a line type of the corresponding cursor, since it becomes easier to match each cursor with the tomographic image. For example, as shown in FIG. 12, in a case where the second tomographic position specification cursor is displayed with a broken line, the display frame of the tomographic image corresponding to the cursor should also be a broken line. It is also possible to match the colors.

(Automatic Move of Index Position)

Furthermore, in the above-described example in FIG. 11, the tomographic position specification cursor 1113 is moved by the operator directly; however, it may also be moved automatically. That is, the display control unit 191 extracts a part corresponding to a lesion from various images generated in step S103, and moves the tomographic position specification cursor 1113 to that position. In extracting the lesion, for example, a DOPU image may be used. In FIG. 13, a reference numeral 1326 denotes an area where the RPE structure is changed, drawn from the DOPU image. In a B scan image where this changed part 1326 exists, the display control unit 191 extracts, for example, a margin of a part where a shape of the RPE changes steeply and moves the tomographic position specification cursor 1113 to that position.

Furthermore, it is also possible to configure such that the retardation map becomes a target of the detection to detect a position where the retardation (a product of a distance and a birefringence in the RNFL) becomes smaller than a predetermined threshold value, and to move the tomographic position specification cursor 1113 to that position. In this case, in a diagnosis of the glaucoma, it is possible to automatically display a part where the RNFL is being damaged. Note that it is possible to set the threshold value through a clinical assessment of an eye to be examined suspected of the glaucoma.

Furthermore, as in the example in FIG. 12 as described above, the initial positions of a plurality of tomographic position specification cursors may be set automatically as described above. In such case, it is possible to cause the above-described standard cursor to be automatically extracted and the other cursor to be movable by the operator, or to cause a positional setting to be automatically performed for both of them.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. the storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-186590, filed Aug. 27, 2012 which is hereby incorporated by reference herein in its entirety.

What is claimed is:

1. An image processing apparatus comprising:
 a planar image acquisition unit configured to acquire a planar image showing a polarization state of a subject;
 a tomographic image acquisition unit configured to acquire a three-dimensional tomographic image including a plurality of two-dimensional tomographic images of the subject;
 a display control unit configured to display, on a display unit, an index indicating a position of a tomographic image to be displayed on the display unit among the plurality of two-dimensional tomographic images by superimposing the index on a planar image showing a polarization state; and
 an instruction unit configured to give an instruction to change a position of the index on the planar image showing the polarization state.

2. The image processing apparatus according to claim 1, wherein
 the display control unit displays, on the display unit, a first index and a second index as the index by superimposing it on the planar image showing the polarization state, and
 the instruction unit gives an instruction to one of positions of the first and the second indexes to change the position of the other one.

3. The image processing apparatus according to claim 2, wherein in a case where the first index is given the instruction from the instruction unit, the instruction unit gives an instruction to change the second index position after the first index has been fixed.

4. The image processing apparatus according to claim 2, further comprising a unit configured to measure a distance of the first and second indexes, wherein
 the display control unit displays a display form indicating the distance on the display unit.

5. The image processing apparatus according to claim 1, wherein, the subject is an eye fundus of an eye to be examined,
 the planar image showing the polarization state is a retardation map, and
 the display control unit displays, on the display unit, a retardation value and a thickness of the RNFL in the eye fundus corresponding to the index position.

6. An image processing method comprising:
 acquiring a planar image showing a polarization state of a subject;
 acquiring a three-dimensional tomographic image including a plurality of two-dimensional tomographic images of the subject;
 displaying, on a display unit, an index indicating a position of a tomographic image to be displayed on the display unit among the plurality of two-dimensional tomographic images by superimposing the index on the planar image showing the polarization state; and giving an instruction to change a position of the index on the planar image showing the polarization state.

7. The image processing method according to claim 6, wherein in the displaying, a first index and a second index are superimposed on the planar image showing the polarization state as the index, and are displayed on the display unit; and
in the giving an instruction, to give an instruction to the position of one of the first and the second indexes to change the position of the other.

8. The image processing method according to claim 7, wherein in a case where the first index is given an instruction, in the giving an instruction, an instruction to change a position of the second index is given after the first index has been fixed.

9. The image processing method according to claim 7, further comprising measuring of a distance of the first and the second indexes,
wherein, in the displaying, a display form indicating the distance is displayed on the display unit.

10. A non-transitory computer-readable medium storing a program configured to cause a computer to execute each step of the image processing method according to claim 6.

11. The image processing method according to claim 6, wherein
the subject is an eye fundus of an eye to be examined,
the planar image showing the polarization state is a retardation map and
in the displaying, a value of retardation and a thickness of the RNFL in the eye fundus corresponding to the index position, are displayed on the display unit.

12. An image processing apparatus comprising:
an eye fundus image acquisition unit configured to acquire an eye fundus image showing a polarization state of an eye fundus of an eye to be examined;
a tomographic image acquisition unit configured to acquire a three-dimensional tomographic image including a plurality of two-dimensional tomographic images of the eye fundus of the eye to be examined;
a display control unit configured to display, on the display unit, a first index, which shows a position of a tomographic image to be displayed on a display unit among the plurality of two-dimensional tomographic images, and a second index different from the first index, by superimposing the first index and the second index on the eye fundus image showing the polarization state; and
an instruction unit configured to give an instruction to change a position of the second index, while in a state where a position of the first index is fixed on the eye fundus image showing the polarization state.

13. The image processing apparatus according to claim 12, further comprising
a unit configured to measure a distance between the first and second indexes, wherein
an eye fundus image showing the polarization state is a retardation map, and
the display control unit displays, on the display unit, a retardation value and a thickness of the RNFL in the eye fundus corresponding to the first and second index position, and a display form showing the distance.

14. An image processing method comprising:
acquiring an eye fundus image showing the polarization state of an eye fundus of an eye to be examined;
acquiring a three-dimensional tomographic image including a plurality of two-dimensional tomographic images of the eye fundus of the eye to be examined;
displaying, on the display unit, a first index, which shows a position of a tomographic image to be displayed on the display unit among the plurality of two-dimensional tomographic images, and a second index different from the first index, by superimposing the first index and the second index on the eye fundus image showing the polarization state; and
giving an instruction to change a position of the second index, while in a state where a position of the first index is fixed on the eye fundus image showing the polarization state.

15. The image processing method according to claim 14, further comprising measuring a distance between the first and second indexes, wherein
the eye fundus image showing the polarization state is a retardation map, and
in the displaying, a retardation value and a thickness of the RNFL in the eye fundus corresponding to positions of the first and the second indexes, and a display form showing the distance, are displayed on the display unit.

16. A non-transitory computer-readable medium storing a program configured to cause a computer to execute each step of the image processing method according to claim 14.

* * * * *